United States Patent [19]

Gorton et al.

[11] Patent Number: 4,490,464

[45] Date of Patent: Dec. 25, 1984

[54] ELECTRODE FOR THE ELECTROCHEMICAL REGENERATION OF COENZYME, A METHOD OF MAKING SAID ELECTRODE, AND THE USE THEREOF

[76] Inventors: Lo G. Gorton, Hantverkaregatan 14, S-211 55 Malmö; Hans Å. Jaegfeldt, Kämpevägen 49, S-151 54 Södertälje; Arne B. Torstensson, Vallkärra 5, S-225 90 Lund; Gillis R. Johansson, Småskolevägen 37, S-223 67 Lund, all of Sweden

[21] Appl. No.: 451,155

[22] PCT Filed: Mar. 8, 1982

[86] PCT No.: PCT/SE82/00059

§ 371 Date: Dec. 2, 1982

§ 102(e) Date: Dec. 2, 1982

[87] PCT Pub. No.: WO82/03729

PCT Pub. Date: Oct. 28, 1982

[30] Foreign Application Priority Data

Apr. 8, 1981 [SE] Sweden .................. 8102242

[51] Int. Cl.³ .................................. B01D 59/40
[52] U.S. Cl. .................................. 435/4; 204/403; 204/290 R; 204/1 T; 429/13; 435/174; 435/175; 435/177; 435/180; 435/817
[58] Field of Search .......... 204/294, 1 E, 403, 290 R; 435/817, 174, 175, 177, 180, 4; 429/13

[56] References Cited

U.S. PATENT DOCUMENTS

| | | | |
|---|---|---|---|
| 3,438,813 | 4/1969 | Davis | 136/83 |
| 3,542,662 | 11/1970 | Hicks | 204/1 E |
| 3,930,884 | 1/1976 | Zimmerman et al. | 136/86 |
| 4,117,202 | 9/1978 | Beck | 429/2 |
| 4,224,125 | 9/1980 | Nakamura et al. | 204/195 |
| 4,304,858 | 12/1981 | Wandrey | 435/11 S |
| 4,321,123 | 3/1982 | Nakamura | 204/403 |

OTHER PUBLICATIONS

Doy et al., "Electrochemically Driven Biochemical Reactions", New York Academy of Science, Transactions vol. 34, 1972, (pp. 588-647).
Chemical Abstracts, vol. 93, (1980), Abstract No. 103772c, Z Phys., Chem. (Wiesbaden), 1980, vol. 120 (1), 39-49.
Chemical Abstracts, vol. 94 (1981), Abstract No. 164733n, Ber. Bunsenges. Phys. Chem., 1981, vol. 85 (3), 221-227.
Angew. Chem., vol. 93, pp. 421-422, published 1981, (Huck H. Schmidt H-L), "Chloranil als Katalysator zur elektrochemischen Oxidation von HADH zu Nad+".
Anal. Chem., vol. 50, pp. 1315-1318, published 1978, (Tse D.C-S., Kuwana T), "Electrocatalysis of Dihydronicotinamide . . . Quinone Electrodes".
J. Electroanal Chem., vol. 113, pp. 151-158, published 1980 (Gorton L. Johansson G), "Cyclic voltammetry of fad adsorbed . . . and gold electrodes".
Anal. Chem., vol. 52, pp. 1691-1697, published 1980 (Blaedel W. J., Engstrom R. C.), "Reagentless Enzyme Electrodes for Ethanol, Lactate, and Malate".
J. of Anal. Chem. USSR, vol. 34, pp. 677-682, published 1979 (Kulis Y.Y., Malinauskas A. A.), "Flow-Type Enzyme Electrode Based on . . . Nicotinamide-Adenine Dinucleotide).
Chemical Abstracts, vol. 91 (1979), Abstract No. 15837f, Dokl Akad, Nauk SSSR 1979, 245 (1), 137-140.
Chemical Abstracts, vol. 93 (1980), Abstract No. 128297q, Anal. Chem. Acta 1980, vol. 117, 115-120.
Chemical Abstracts, vol. 93 (1980), Abstract No. 3074h, Jpn. Kokai Tokkyo Koho 80 13,072.

*Primary Examiner*—John F. Niebling
*Attorney, Agent, or Firm*—Shapiro and Shapiro

[57] ABSTRACT

Electrodes for the electrochemical regeneration of the co-enzymes, NADH, NADPH or analogs thereof. The electrode surface has been modified by adsorbing thereto a condensed aromatic ring system comprising at least three, preferably four or more, condensed aromatic rings. A method of preparing the electrodes is also described, in which a condensed aromatic ring system is adsorbed to the surface of carbon or a graphitic material. Finally, there is described the use of said electrodes for the electrochemical regeneration of co-enzyme in biochemical, microbiological or biochemical processes as the anode in biochemical fuel cells or for analysis in systems utilizing co-enzyme-dependent enzyme.

9 Claims, 15 Drawing Figures

I

II

III

IV

I

II

X = N, O, S

Y = NR$_2^+$, O a b c d

ELECTRODE FOR THE ELECTROCHEMICAL REGENERATION OF COENZYME, A METHOD OF MAKING SAID ELECTRODE, AND THE USE THEREOF

TECHNICAL FIELD

The invention relates to electrodes, perferably of graphite, the surface of which has been so modified that an electrochemical oxidation of co-enzyme or co-enzyme analogs occurs at the electrode surface with far greater ease than at an unmodified electrode surface. The modification implies that mediator molecules which are described in more detail below, are immobilized on the graphite by spontaneous adsorption.

The invention described may be used for regenerating the co-enzymes in different biotechnical, microbiological or biochemical processes. Regeneration is effected electrochemically at the surface of the electrode described; the circuit is closed by means of a counter-electrode of known type. Improved supervision is obtained if also a reference electrode is provided and a potentiostatic circuit is utilized.

The electrodes according to the present invention may also be utilized as the anode in so-called biochemical fuel cells, in which case the cathode is an electrode of known type, such as an oxygen or air electrode. Within the cell, a substrate, for example alcohol, is oxidized by enzyme catalysis, whereby the co-enzymes are reduced. The resulting, reduced co-enzymes can be oxidized at the modified electrode surface, and the half-cell can supply an electric current.

Furthermore, the modified electrodes according to the invention may be utilized in analysis systems together with co-enzyme-dependent enzyme. The analysis method may be utilized for the analysis of different substrates, depending upon the choice of enzyme. The modified electrode can supply a current which is approximately proportional to the substrate content of the sample. Measurement may also be effected potentiometrically, in which case the electrode potential will be approximately proportional to the logarithm of the substrate content in the sample.

BACKGROUND

Enzyme-catalysed reactions of the type

Substrate + (1)

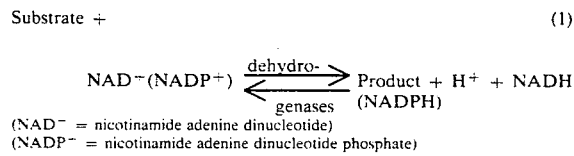

(NAD<sup>-</sup> = nicotinamide adenine dinucleotide)
(NADP<sup>-</sup> = nicotinamide adenine dinucleotide phosphate)

play an important part in biological cells and in biotechnical and analytical reactions. Several hundreds of different hydrogenasas are known which selectively catalyse the conversion of different substrates into products. When the substrate is oxidized, the co-enzymes NAD+ and NADP+, respectively, are at the same time reduced to NADH and NADPH, respectively. The major part of the hydrogenases make highly specific demands on the co-enzyme, for which reason NAD+ and NADP+, respectively, are necessary to bring about a reaction.

The co-enzymes NAD+ and NADP+ are very expensive chemicals which are difficult to obtain. The possibilities of regenerating them by reoxidation therefore are of great economical importance. Regeneration may also be necessary for displacing the equilibrium (1) to the right. In this manner, the substrate can be completely converted into a product, which facilitate the isolation or increase the yield of the desired synthesis products. The displacement may also be a prerequisite for the analytical use of the reaction.

Co-enzyme may be regenerated in different ways:
(a) Chemical regeneration

Oxidation of co-enzymes with retained activity can be effected only with certain specific oxidizing agents. Such compounds are frequently termed mediators. In FIG. 1, compounds I (phenazine methosulphate, PMS), II (phenazine ethosulphate, PES), III (thionine) and IV (1,2-benzoquinone) are examples of known mediators.

Hitherto known mediators have been used to a limited extent because they, too, are expensive and their stability in the solution may be low. Furthermore, difficulties may arise when the mediators on their reaction and decomposition products are to be isolated from the desired product.

(b) Enzymatic regeneration

Use is made of an auxiliary reaction, for instance the following:

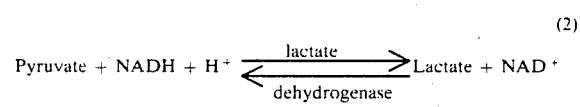

(2)

Besides the enzyme according to equation (1), the enzyme lactate dehydrogenase must be added which catalyses a reaction in the opposite direction. If pyruvate is added in excess, NAD+ will be regenerated.

The use of two separate enzymes makes the biotechnical process more complicated. The reagent of the auxiliary system is mixed with the desired products.

(c) Electrochemical regeneration

The co-enzyme may be regenerated according to the following reactions:

  (3)

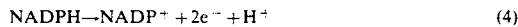  (4)

Studies of the electrochemical oxidation of NADH have been reported by H. Jaegfeldt in the Journal of Electroanalytical Chemistry, Vol. 110, p. 295 (1980), by J. Moirouz and P. J. Elving, Analytical Chemistry, Vol. 47, p. 1337 (1975). At pH 7.0, the standard electrode potential of the redox pair NADH/NAD+ is −0.32 V measured against a standard hydrogen electrode (NHE). The standard electrode potential of NADPH/NADP+ is almost equally high.

Thermodynamically, the major part (99%) of the co-enzyme could be reacted at an electrode potential which is more anodic than the standard potential by 60mV, i.e. at −0.26 V against NHE. In actual practice, an overvoltage of at least one volt is required for platinum electrodes, while graphite electrodes require an overvoltage immediately below one volt (at least 0.7–0.9 V against NHE). The platinum electrodes require careful pretreatment to prevent side reactions and to give enzymatically active NAD+ (see H. Jaegfeldt, A. Torstensson and G. Johansson, Analytical Chimica Acta, Vol. 97, p. 221 (1978)). Later studies show that NADPH acts in essentially the same manner as NADH during electrochemical oxidation.

The high overvoltage entails considerable disadvantages. Because the electrode is highly oxidizing, substrates, products, enzymes or other components in the test solution may react in an undesired manner. The enzyme may be denaturized by the high potential. Higher contents of co-enzyme cause side reactions at the electrode surface. The character of these reactions has not been investigated, but it is known that they poison the electrode so that the main reaction is decelerated or discontinued. Different reaction products may polymerize into films inactivating the electrode. Unmodified graphitic materials catalyse a decomposition of the co-enzyme (A. Torstensson, G. Johansson, M-O Månsson, P. O. Larsson and K. Mosbach, Analytical Letters, Vol. 13 B (10)).

Many soluble mediators may be reoxidized electrochemically without excessive overvoltages and may, thus, be used in an auxiliary system for electrochemical regeneration.

In addition to the disadvantages already mentioned and caused by the mixing of the mediator with the reaction products, further difficulties frequently arise because the reduced form of the mediator is difficultly soluble and precipitates.

PRIOR ART (MODIFIED ELECTRODE SURFACES)

D. C. S. Tse and T. Kuwana (Analytical Chemistry, Vol. 50, p. 1315 (1978)) oxidized a graphite surface in oxygen plasma and reduced the oxygen functionalities into OH-groups with $LiAlH_4$, to which 3,4-dihydroxybenzylamine was then coupled by trichlorotriazine. The electrode thus modified was capable of oxidizing NADH at lower anodic potential (about +0.5 V against NHE) than an unmodified graphite electrode. However, the life of this electrode amounted to but a few operating cycles. The surface covering, i.e. the number of mediating groups per unit area, was low, and consequently also the current density of the electrode became very low.

C. Degrand and L. L. Miller (Journal of the American Chemical Society, Vol. 102, p. 5728 (1980)) made a modification residing in that a polymer containing mediating groups was absorbed to a surface of glassy carbon. Dopamine was copolymerized with poly(methacryloyl chloride).

The life of this electrode type was somewhat higher, i.e. about ten operating cycles. The electrode potential for reoxidation of the mediator had been lowered by 50 mV as compared with the Tse and Kuwana had achieved. The total overvoltage of the NADH oxidation was slightly below 0.8 V. Also the surface covering had been improved.

Earlier works have shown that certain substances containing the isoalloxazine ring can be adsorbed to graphite (L. Gorton and G. Johansson, Journal of Electroanalytical Chemistry, Vol. 113, p. 151(1980)). The electron transfer between the adsorbed compound and the electrode material was rapid, and the adsorbed compound (flavin adenine dinucleotide, FAD) could be reduced and oxidized an unlimited number of times. Electrodes, on which FAD or other flavines had been adsorbed, exhibit no catalytic effect for the electronic yield with NADH.

GENERAL DESCRIPTION OF THE INVENTION

The present invention comprises electrodes modified in such a manner that the electrochemical oxidation of NADH, NADPH, NADH analogs or NADPH analogs is catalysed. The electrodes are characterized in that there has been imparted to the electrode surface a mediator function in that a condensed aromatic ring system comprising at least three, preferably however four or more condensed aromatic rings with or without hetero atoms, has been adsorbed to the electrode surface. The ring system may be substituted, and side chains are no obstacle. Adsorption occurs spontaneously from a solution containing the compound. The invention also is characterized in that the electron exchange with the co-enzyme or the co-enzyme analog is effected via structural elements comprising either one of alkyl phenazinium ions (I in FIG. 2), phenazinium ions (II in FIG. 2, $X=N$, $Y=NR_2^+$), phenazinones (II in FIG. 2, $X=N$, $Y=O$), phenoxazinium ions (II in FIG. 2, $X=O$, $Y=NR_2^+$), phenoxazones (II in FIG. 2, $X=O$, $Y=O$), phenothiazinium ions (II in FIG. 2, $X=S$, $Y=NR_2^+$), phenothiazinones (II in FIG. 2, $X=S$, $Y=O$). In all cases, the molecules may be substituted in the rings in the manner explained below, or be condensed with further aromatic rings, substituted or unsubstituted. Substitutents may be so selected that the overvoltage is further reduced (preferably amines, alkyl groups and alkoxy groups). In alternative embodiments of the invention, alkyl phenazinium ions, phenazinium ions, phenazinones, phenoxazinium ions, phenoxazines, phenothiazinium ions, phenothiazones may be inserted in side chains which are connected by at least one carbon atom to an adsorbed polyaromatic ring system. Furthermore, the electrode material in the context of this invention is graphite or carbon.

The invention also comprises a method of preparing the electrode by adsorbing the condensed aromatic ring system on the surface of carbon or a graphitic material.

Finally, the invention also comprises the use of electrodes for the electrochemical regeneration of co-enzymes in biotechinical, microbiological or biochemical processes, as the anode in the biochemical fuel cell, which cell operates with dehydrogenases as catalysts and with co-enzyme as energy-transferring redox pair, or for analysis in systems utilizing co-enzyme-dependent enzyme.

As will be seen, the current attains a maximum value when the rotational speed is increased. This is expected in an experiment involving a rotary disk electrode, when the current is entirely under kinetic control. The maximal value is determined both by the coating of Meldola's Blue on the electrode and by the NADH content of the solution. The step determining the velocity is the reaction with the soluble NADH and immobilized Meldola's Blue.

Figure 7:
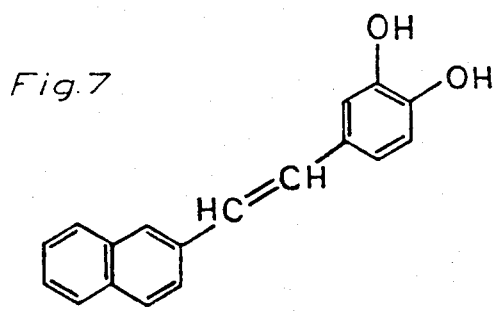

FIG. 7 illustrates the structural formula of naphthalene stilbene catechol.

Figure 8:
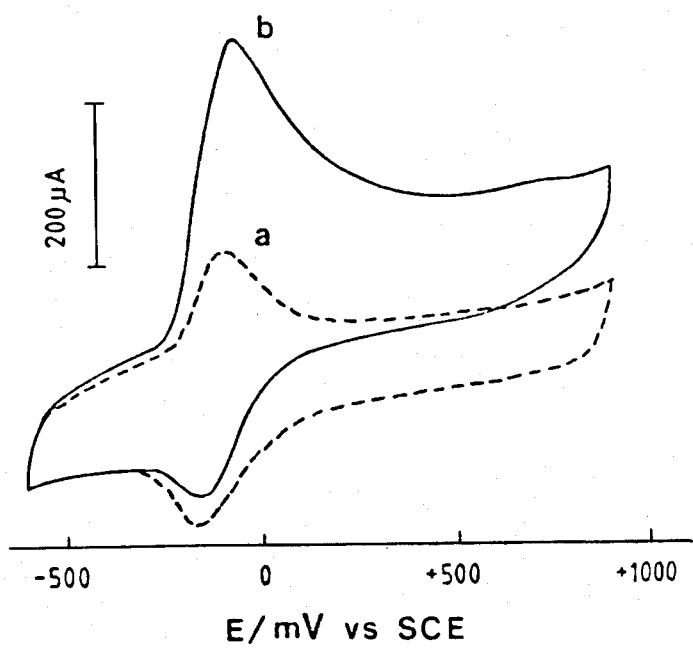

FIG. 8 illustrates cyclic voltammograms with a phenazine methosulphate-modified graphite electrode without NADH in the solution (a) and in a 5 mM NADH solution (b). The experiments were conducted in a 0.1 M phosphate buffer solution, pH 7.0.

Figure 9:
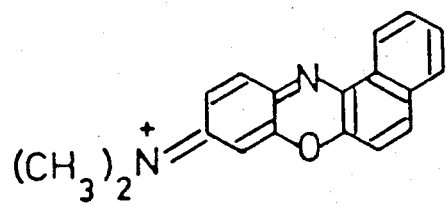

FIG. 9 illustrates the structural formula of Meldola's Blue (MB, 7-dimethylamino-1,2-benzophenoxazinium).

Figure 10:
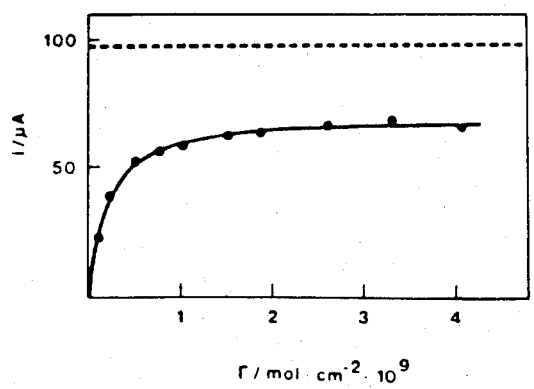

FIG. 10 illustrates the catalytic current of a rotary MB-modified graphite electrode as a function of the surface covering. The dash line shows the theoretical value of an infinitely rapid chemical reaction. The concentration of NADH was 2.91 mM, pH 7.0. The angular velocity was 99 radians/s.

Figure 11:
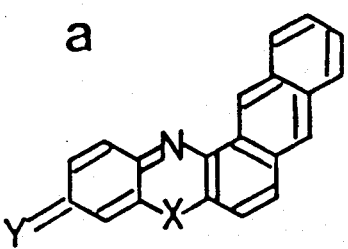
Figure 11:
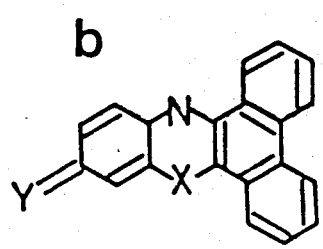
Figure 11:
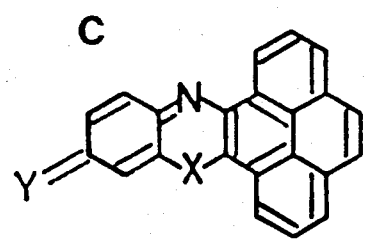
Figure 11:
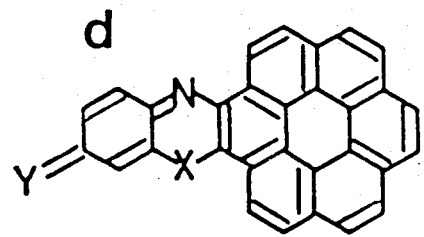

FIG. 11 exemplifies how further rings may be condensed to Meldola's Blue (X=O, Y=N(CH$_3$)$_2^+$).

Figure 12:
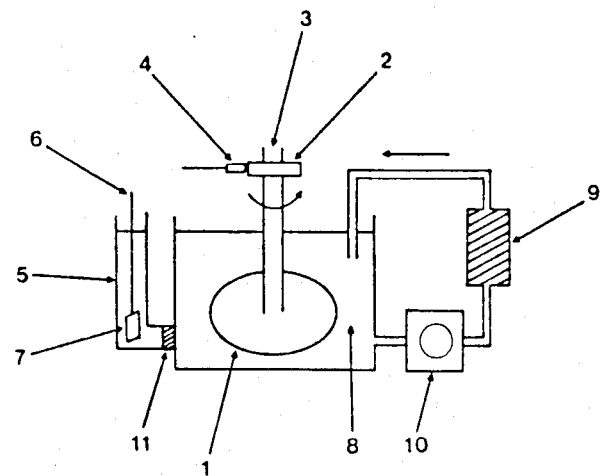

FIG. 12 illustrates an embodiment of the invention for biotechnical use of a modified graphite electrode.

Figure 13:
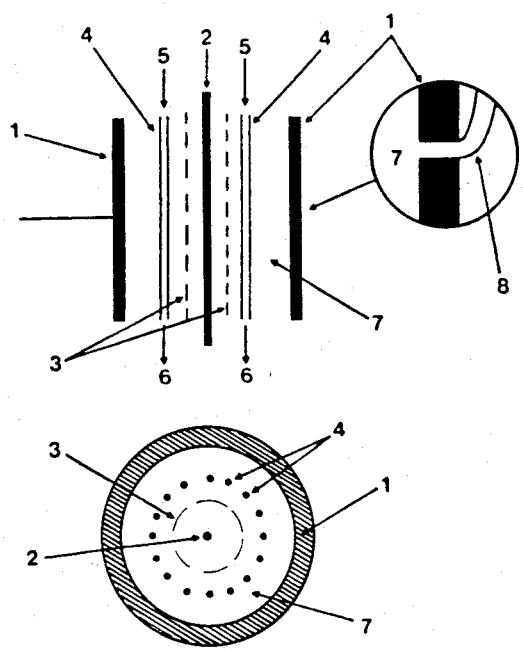

FIG. 13 illustrates another embodiment of the invention for biotechnical use of the mediator-modified graphite electrode (1).

Figure 14:
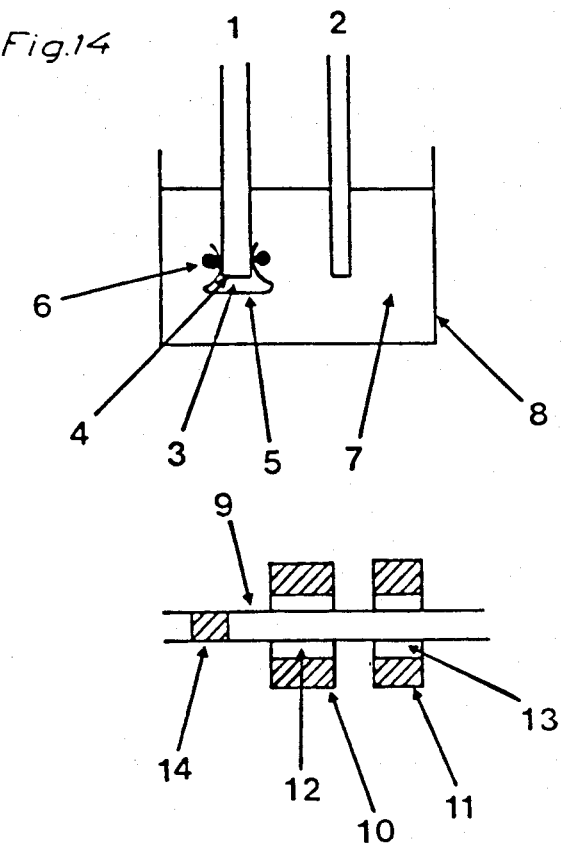

FIG. 14 illustrates an embodiment of the invention for the analysis of substrates.

Figure 15:
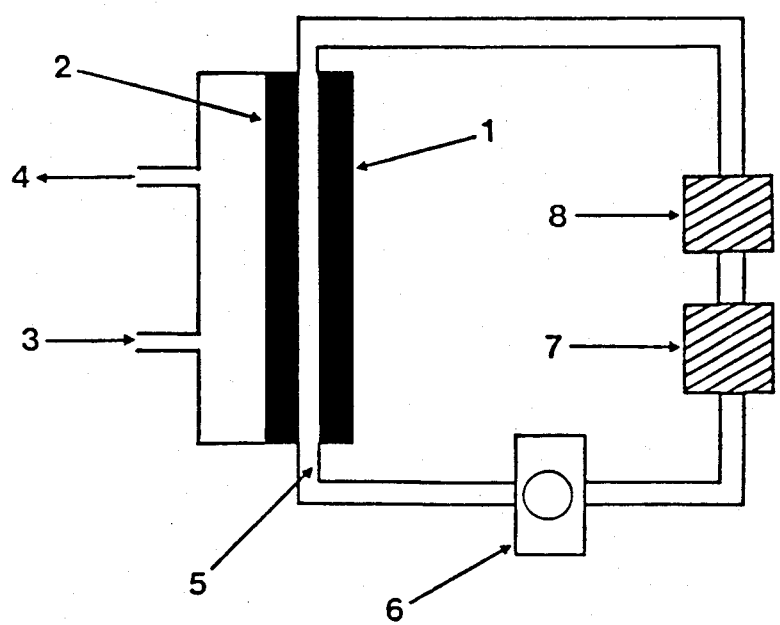

FIG. 15 illustrates an embodiment of the invention when the mediator-modified graphite electrode is utilized in biochemical fuel cells for the production of electric energy.

DETAILED DESCRIPTION OF THE INVENTION

Anchoring to graphite

Modification of an electrode surface requires, on the one hand, that the functionalities intended can be attached to the electrode surface and, on the other hand, that electron transfer can be effected rapidly all the way down into the electrode material. A number of quinones were selected as model substances because it is possible to test, in a simple manner, both the strength of the adsorption and the electron exchange between the quinone functionality and the graphite.

The prior art technique in connection with electrochemical investigation methods is disclosed by the book "Electrochemical Methods, Fundamentals and Applications" by A. J. Bard and L. R. Faulkner (J. Wiley & Sons, 1980). If the electrode voltage increases linearly with time and then is reversed and decreases linearly with time, a cyclic voltammogram is obtained (see FIG. 4). The area below the anodic or cathodic peak, corrected in regard to the background, is a measure of the amount of substance that has been oxidized or reduced. The peak potential can be related to the standard electrode potential by prior art technique. The distance along the voltage axis between the anodic and the cathodic peak, and the variation of this distance with the sweep rate, provide information about the rate of the electrochemical reactions. It is possible to decide, from the shape of the curve, whether the substance is adsorbed to the surface or whether it is present in the surrounding solution and is conveyed by diffusion. Double peaks indicate that the process takes place in distinctly separated steps.

An about 1 mM solution of said quinone or hydroquinone dissolved in buffer was prepared. A graphite rod (graphite electrode) was immersed in the solution for some time and then removed therefrom and carefully washed. It was then immersed in a buffer solution without the addition of quinone, whereupon a cyclic voltammogram was recorded for the electrode in question. The amount of substance remaining on the electrode after washing and transfer was determined from the area of the curves. New voltammograms were recorded at certain time intervals to see if, in course of time, the substance was dissolved out from the electrode.

Figure 3:
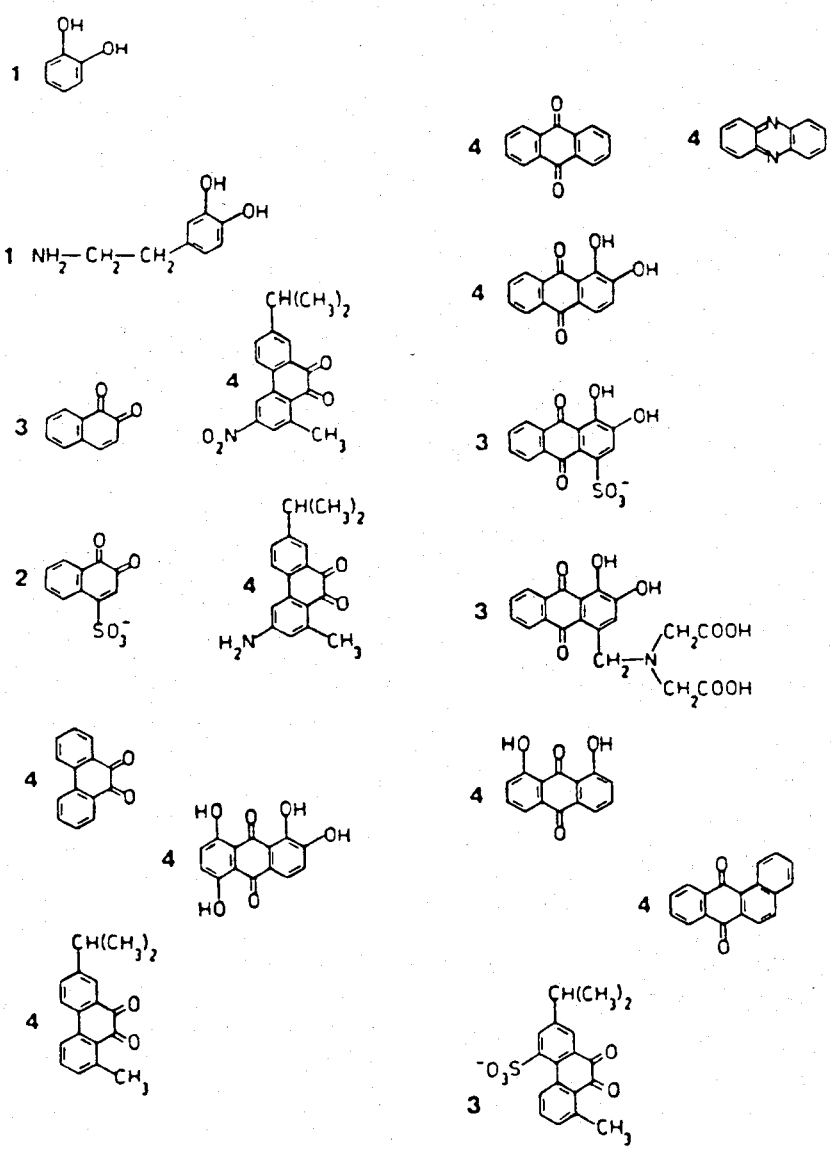
FIG. 3 illustrates the structural formulae of the quinones and a heterocyclic compound whose adsorption characteristics on graphite were investigated. The compounds of class 1 are not adsorbed to any appreciable degree. Class 2 is adsorbed to a slight degree and is quickly dissolved out. Class 3 is adsorbed to a greater degree and is dissolved out more slowly, and class 4 is adsorbed to a considerable degree and is but slowly dissolved out.

FIG. 3 illustrates the quinones that were investigated, and also a heterocyclic compound. They were classified in four groups. Quinones that were not adsorbed to any appreciable degree, were referred to group 1, quinones that were adsorbed to a slight degree and quickly dissolved out, were referred to group 2, quinones that were adsorbed to a greater degree and were dissolved out more slowly, were referred to group 3, and finally quinones and the heterocyclic compound that were adsorbed to a considerable degree and slowly dissolved out, were referred to group 4. The numbers next to the compound indicate the class to which the compound belongs.

The material shows that the adsorption of quinones having a single aromatic ring is but slight, but that the adsorption is increased when the ring number increases. Functional groups entailing increased water solubility reduce the adsorptive power. To obtain a strong adsorption, the ring system must attain a given size, and the water solubility must be low.

The invention is based upon the discovery that compounds containing a mediator function can be attached to the electrode surface by adsorption in such a manner that rapid electron transfer is achieved. This immobilization method is basically different from the covalent binding technique reported by Tse and Kuwana. The adsorbed quinones shown in FIG. 3 catalyse the coenzyme oxidation at a very slow rate.

Naphthalene stilbene catechol electrode, NSCH$_2$ electrode

Figure 4:
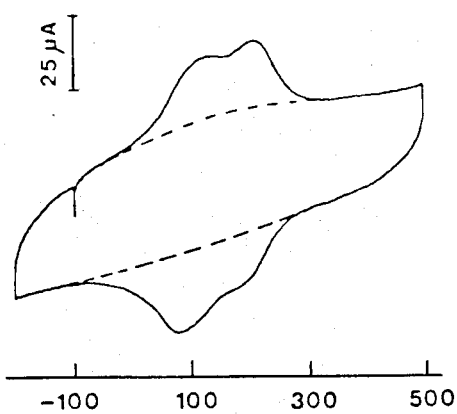
FIG. 4 illustrates a cyclic voltammogram of the graphite electrode prior to modification (dash line) and after modification with naphthalene stilbene catechol (full line). The voltammograms are recorded in a 0.1 M phosphate buffer, pH 7.0, with a sweep rate of 50 mV/s.

A naphthalene stilbene catechol, FIG. 7, was synthetized and, since the water solubility of NSCH$_2$ is low, an about 0.05 mM solution in about 50% ethanol was prepared. The tip of a graphite rod, $\phi = 6.15$ mm, was immersed in the solution for about 10 min. The graphite rod was taken out, washed and transferred to a buffer that did not contain $NSCH_2$. The graphite rod thus modified is termed the $NSCH_2$ electrode. FIG. 4, the dash line, shows a cyclic voltammogram of the graphite rod prior to modification, and FIG. 4, the full line, shows a cyclic voltammogram for the $NSCH_2$ electrode after modification. The greater area of the latter curve shows that the electrode surface is coated with a redox pair. The coating was calculated at $5.10^{-9}$ mole/cm$^2$. Two separate electron transfer steps may be noted.

Figure 5:
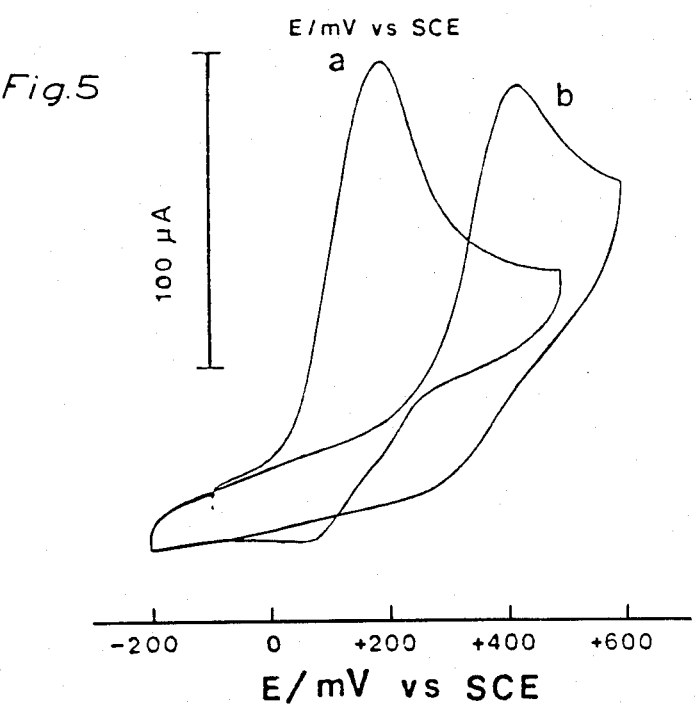
FIG. 5 illustrates cyclic voltammograms of a graphite electrode modified with naphthalene stilbene catechol (curve a) and an unmodified graphite electrode (curve b) in a 0.1 M phosphate buffer, pH 7.0, containing 2.2 mM NADH, with a sweep rate of 50 mV/s.

The $NSCH_2$ electrode was then transferred to a new buffer containing 2.2 mM NADH, pH 7.0. It appears from the voltammogram of this solution (FIG. 5, curve a) that the anodic current has increased, and that the cathodic current has decreased as compared with the voltammogram of the $NSCH_2$ electrode in pure buffer without NADH (FIG. 4, full line). This is due to the fact that the dissolved NADH reduces the mediator group (the catechol of FIG. 7) while the voltage sweep is in progress. The electrochemical reoxidation of the mediator group requires current, which explains the increase of the anodic current. The decrease of the cathodic current is explained in analogous manner; NADH in the solution reduces certain mediator groups, such that fewer groups need be reduced electrochemically. The catalytic efficiency of the $NSCH_2$ electrode is directly apparent from FIG. 5, if curve a is compared with curve b. Thus, the latter curve has been recorded with an unmodified graphite rod in the same solution. The decrease of the overvoltage for electrochemical oxidation of NADH, slightly more than 200 mV, can be read directly on the Figure. At pH 9.0, the reduction is slightly more than 300 mV.

The experiments conducted with the $NSCH_2$ electrode illustrate how the attachment of a substance can be effected, and how in that case the reaction rate is increased by raising of the active group from the surface. However, the reduction of the overvoltage that can be effected by means of the catechol group is not sufficient. The life is limited because the naphthalene group is rapidly desorbed. Experiments conducted with a pyrene group have shown that, when the ring system is enlarged, the desorption will be insignificant.

Phenazine methosulphate electrode, PMSH electrode

Figure 1:
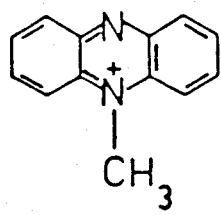
FIG. 1 illustrates structural formulae of phenazine methosulphate (I), phenazine ethosulphate (II), thionine (III) and 1,2 benzoquinone (IV).
Figure 1:
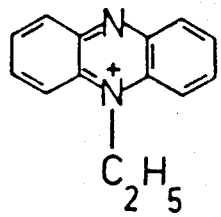
Figure 1:
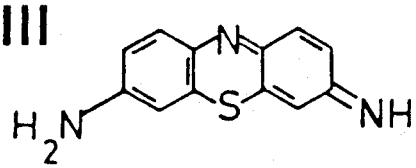
Figure 1:
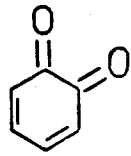
Figure 2:
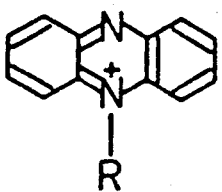
FIG. 2 illustrates the basic structure of alkyl phenazinium ions (I, R = alkyl group), phenazinium ions (II, $X=N$, $Y=NR_2^+$), phenazinones (II, $X=N$, $Y=O$), phenoxazinium ions (II, $X=O$, $Y=NR_2^+$) phenoxazinones (II, $X=O$, $Y=O$), phenothiazinium ions (II, $X=S$, $Y=NR_2^+$), phenothiazinones (II, $X=S$, $Y=O$). In group II R may be H and/or an alkyl group.
Figure 2:
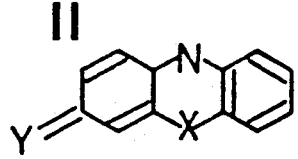

Phenazine methosulphate, I in FIG. 1, was adsorbed from an about 1 mM aqueous solution for about 15 min. on a graphite rod. The rod was taken out, washed and mounted as electrode in a solution which did not contain PMS. FIG. 8, curve a, shows the voltammogram obtained at pH 7. The standard electrode potential for PMSH/PMS$^+$ extends much further in the negative direction than for the above-mentioned compounds containing 1,2-quinone functionality. The peak potential lies at about 0.19 V (measured against NHE). FIG. 8, curve b, also shows the voltammogram obtained when the electrode was immersed in a buffer containing 5 mM NADH. The anodic peak then is greatly increased, while the cathodic peak is reduced. The course of the reaction was as follows:

(5)

(6)

(7)

Equation (6) was far more rapid than equation (5). The net reaction, equation (7), implies that NAD$^+$ is regenerated by the intermediary of the immobilized mediator, PMS$^+$. The life of the PMSH electrode was longer than that of the $NSCH_2$ electrode.

Phenazine, i.e. a molecule having no substituent on nitrogen, is also adsorbed to graphite, but has no electrocatalytic activity.

The phenoxazinium electrode, the MB electrode 7-dimethylamino-1,2-benzophenoxazinium (Meldola's Blue), MB$^+$, FIG. 9, was dissolved in water and adsorbed on graphite, as explained above. The compound has previously been used as a mediator (DE OS 1,959,410). It was investigated by cyclic voltammetry in the same way as above. $E_{\frac{1}{2}}$ for the adsorbed compound was +70 mV against a normal hydrogen electrode. Like above, the first step involved a chemical reaction (velocity constant $6.10^3 M^{-1}s^{-1}$)

(8)

(9)

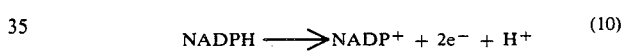
(10)

The second step was a much more rapid electrochemical oxidation of the mediator.

Figure 6:
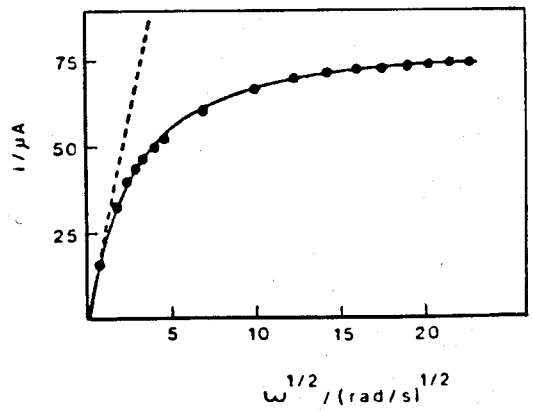
FIG. 6 illustrates the result when a graphite electrode is modified with Meldola's Blue (MB) and investigated with rotary disk electrode technique and when the potential is kept highly oxidizing in relation to the Meldola's Blue half-wave potential. A rectilinear relationship between the current magnitude and the root of the rotational speed of the electrode is expected if NADH is oxidized infinitely rapidly (dash line). The full line shows the above-mentioned relationship in a 7 mM NADH solution when the electrode has been coated with $4.4 \cdot 10^{-10}$ mole/cm$^2$. The experiment was conducted in a 0.1 M phosphate buffer, pH 7.0.

FIG. 6 illustrates the results obtained with a different investigation method called rotary disk electrode. The electrode is mounted for uniform and vibration-free rotation by means of a motor, the rotational speed of which is variable and known. At higher rotational speeds, $\omega$, the dissolved substances are conveyed much more rapidly. The dash line in FIG. 6 shows which current would have been obtained theoretically (at a highly oxidative potential) at different rotational speeds, if the co-enzyme had reacted infinitely rapidly (equation 8), while the full line shows the current actually obtained. The position on the plateau makes it possible to determine the velocity constant for equation 8.

The amount of MB$^+$ adsorbed on the graphite rod was varied by varying the immersion time in the MB$^+$ solution. The amount could be determined from the integral of a cyclic voltammogram. FIG. 10 shows how the catalytic activity is changed with the amount of adsorbed substance $\Gamma$. The dash line shows the catalytic activity that would have been obtained if equation (8) had been infinitely rapid. The experiment was made with rotary electrodes. It is seen that the electrocatalysis of the co-enzyme oxidation initially increases with the amount of MB$^+$ and then flattens out. The plateau corresponds to a multilayer covering with MB$^+$. Only the top layer is catalytically active since the co-enzyme is unable to react with deeper layers. Electrons, on the other hand, can pass through different MB$^+$ layers down to the graphite.

The adsorption of MB to graphite is much stronger than that of PMS or PES because the number of aromatic rings is greater, since the strength of the adsorption increases when several $\pi$ electrons from the adsorbed molecule overlap the $\pi$ electron orbitals from the graphite. MB also has a higher chemical stability and is less light-sensitive than PMS and PES. It is, however, unstable in strongly alkaline solution.

Substances which are sparingly soluble in water can be dissolved for instance in water/alcohol, or in a purely organic solvent. The graphite surface can also be coated in the dry state by rubbing in the substance entirely mechanically.

It is more advantageous to use graphite or carbon than so-called glassy carbon. The latter material gives a lower surface covering. So-called Teflon graphite, i.e. a mixture of finely divided graphite with finely divided Teflon, is less suitable since the electrode transfer between the aromatic ring system and the electrode material is slower than if pure graphite is used.

Suitable mediator molecules

The strength of the adsorption increases with the number of rings participating in the binding to the graphite. If further rings are condensed to for example MB, FIG. 11, the desorption rate can be further reduced. These rings can be placed rather randomly; see FIGS. 11 a–d. The substituent can affect $E^o$, as well as the solubility, i.e. desorption, and the chemical stability. Amines, alkyl groups and alkoxy groups reduce $E^o$, while halogens, carboxylic acids, aldehydes and nitro groups should be avoided since they are expected to raise $E^o$. The reactive group, the mediator group, may be combined with the adsorbed ring system via a carbon chain, in which case the mediator group is expelled from the graphite by the stronger adsorption of the larger ring system.

Effects of medium

The electrode potentials indicated in the different descriptions refer, unless otherwise stated, to pH 7.0 and a buffer consisting of 0.1 M phosphate. Changes in the composition of the medium, i.e. the type of other ions, the ionic strength and the pH, result in conventional manner in changes in the electrode potentials measured. The displacement will be especially pronounced if any of the medium ions can affect an equilibrium in which the reactants are included. By consciously selecting the electrolyte composition, the oxidation of co-enzyme can thus take place closer to the reversible potential of the co-enzyme.

$NADP^+$ regeneration

The above descriptions of the different modified electrodes are but a selection of the experiments made and merely serve to illustrate the invention. In several cases, corresponding experiments have been conducted with both NADPH and with NADH. The results have throughout been practically identical. Thus, the electrodes described can be used for the electrochemical regeneration of $NADP^+$.

$NAD^+$ and $NADP^+$ analogs

In a biotechnical process in which the co-enzyme is to be reused, it must be possible to separate these analogs from the products removed from the process. Also in analytical applications, it is frequently advantageous to prevent the co-enzymes from mixing with the test solutions and getting lost. In the latter applications, the co-enzymes can be retained by dialysis membranes with very fine pores. However, the permeability of these fine membranes to reactants of other types is low and frequently insufficient for process purposes. To improve the possibilities of retaining the co-enzyme functionalities, it is possible synthetically to increase the molecular size by binding the co-enzymes to an inert polymer. To retain the co-enzyme function, substituents are allowed, in most cases, only in the adenine ring. Dolabdjian and coauthors report in "Enzyme Engineering", Vol. 4, p. 399 (1978) a method of increasing the molecular weight by couplings to modified dextrans.

It has been found that modified electrodes according to the present invention are capable of regenerating such co-enzyme analogs. The velocity is expected to decrease with the diffusion coefficient raised to $\frac{2}{3}$. Since the diffusion coefficient is low for coenzyme analogs with large polymer groups, the current is reduced considerably. No exact checks were made to establish whether the behaviour of the analogs follows the theory, because their diffusion coefficients are not known. A specific form of co-enzyme analog is obtained if two co-enzymes are bonded together. In another embodiment, the co-enzymes have been bonded to the enzyme.

EXAMPLES OF EMBODIMENTS

Example 1

FIG. 12 illustrates a modified electrode according to the invention in the form of a rotary graphite disk 1 secured to a shaft 3 and provided with a sliding contact 4 engaging the disk 2. The graphite disk constitutes the electrode according to the invention. Disposed on the cell is a side chamber 5 containing the counterelectrode 7. The side chamber is in electrically conductive connection with the main chamber, but the reaction products are prevented from entering said main chamber by a partition 11 which may consist of a dialysis membrane or a sintered glass filter. The solution 8 contains a buffer, NADH, and a substrate of some type. The reactor 9 contains an enzyme which has been immobilized by prior art technique on a carrier, such as porous glass. The pump 10 pumps the solution 8 through the enzyme reactor and back to the electrolysis cell.

Between the electrodes 1 and 7, there is applied a voltage having the polarity indicated and such a magnitude that the modified graphite electrode 1 is capable of oxidizing NADH. A current passes through the circuit. The current (in ampere) is indicated approximatively by the number of moles of regenerated $NAD^+$ per unit of time, multiplied by the factor 193,000. (193,000 = Faraday's constant $\times$ 2). The concentration of $NAD^+$ in the solution 8 thus increases in time. The solution already contains the substrate, and thus a reaction according to equation (1) can be started in the enzyme reactor 9. The substrate is converted into the desired product, and the process can proceed continuously. When no more substrate is available, or when the desired product content has been achieved, the product can be isolated from the electrolyte 8 by known methods, whereupon the experiment can be repeated without necessitating the supply of new co-enzyme. Such isolation of the product may also be effected continuously by known methods.

In another embodiment, the enzyme is dissolved or suspended in the electrolyte 8 (in which case the reactor 9 and the pump 10 may be dispensed with).

In another embodiment, a mediator has been immobilized on the surface of the electrode 1 in accordance with the present invention. Furthermore, a mediator in dissolved form has been added to the electrolyte 8. In this manner, the life of the modified electrode 1 can be prolonged because a new mediator can be absorbed directly from the reaction solution. A mediator reservoir can also be accomplished by mixing the graphite with the mediating substance during production, or by filling the pores in the graphite with mediator substances in accordance with the invention.

In another embodiment, the modified graphite electrode is stationary, and the electrolyte is instead stirred magnetically or by a propeller, to such an extent that a sufficient mass transfer is achieved.

In one embodiment, the co-enzyme has been attached to the enzyme for instance in the manner described in the previously reported work in "Analytical Letters", whereupon the enzyme-co-enzyme complex is placed adjacent the electrode surface or immobilized thereon, together with the above-mentioned mediator functionalities.

The selection of the enzyme, the immobilizing method or the dispersion form, and also the pH and the composition in other respects of the electrolyte, may vary within a large range. These selections are conditioned by known aspects in order to optimize a biotechnical process.

Example 2

FIG. 13 illustrates an embodiment of the invention in which a cylindrical graphite electrode 1 has been modified in accordance with the invention. A counterelectrode 2 which may consist of a graphite rod, has been placed in the centre. The co-enzyme can be prevented from contacting the counterelectrode by a membrane or a dialysis hose 3. A bundle of dialysis fibres 4 passes through the cell. Substrate solution is pumped into the inlet 5 of the dialysis fibres, and a product solution is obtained at the fibre outlet 6. The electrolyte 7 contains a buffer, a co-enzyme such as $NAD^+$ and NADH or $NADP^+$ and NADPH, or analogs thereof. Provisions for stirring the electrolyte may also be made. Several embodiments are conceivable. The enzyme may be dissolved or dispersed within the electrolyte 7. It may be immobilized on the modified electrode 1 together with the immobilized mediator. The electrolyte 7 may also contain a low content of mediator, preferably less than 0.05 mM.

When the substrate is pumped through the dialysis fibre, it is discharged through the fibre pores into the electroyte 7 and conveyed to the enzyme which has been disposed according to one of the above-mentioned possibilities. If an oxidized cofactor is available, the substrate is converted into product. The reduced cofactor which is then formed, will be regenerated at the modified graphite electrode 1, such that the reaction according to equation (1) may proceed. The resulting product diffuses into the dialysis fibre so that the product content will be high and the substrate content low at the outlet 6. If a high degree of conversion is desired, it may be necessary to make the apparatus much larger in the axial than in the radial direction. In that case, difficulties may arise in keeping the electrode 1 active throughout its extent. The reaction rate is the highest and the current will therefore be the strongest adjacent the inlet 5. The strongest polarization of the counterelectrode 2 occurs in that part which is closest to the inlet, and therefore it will be impossible to maintain the correct potential difference both at the inlet and at the outlet. The counterelectrode can therefore be divided into sections, each section being provided with a separate electrical connection. To facilitate checking that the electrode 1 has the correct potential, one or preferably two or more reference electrodes are utilized. An enlargement shows how a fine tube or hose 8 can be inserted through the wall of the graphite electrode. This tube or hose is in electrolytical connection with the reference electrode of conventional type, such as a calomel electrode. A known electronic apparatus, termed potentiostat, requires connection of both the reference electrode, the working electrode 1 and the counterelectrode 2. The potentiostat will then control the current through the counterelectrode or a segment of said counterelectrode until the potential difference between the reference electrode and the working electrode 1 shows the set value. If the counterelectrode is divided into sections, each such section must have a potentiostat.

In one embodiment, the modified electrode 1 is porous in order to increase the surface area and, thus, the reaction rate. An especially large surface area can be obtained if a felt of graphite fibres is used and formed in such a manner that it more or less completely fills out the electrode space with the electrolyte 7. The amount of enzyme can also be increased by the attachment of different matrix types, for example inside the pores of porous glass. This will also prevent contact between the electrode an the enzyme, which may be of importance to certain dehydrogenases. In this manner, the regeneration plant can be given a compact shape in the radial direction. If highly porous materials are employed, it will be necessary either to provide a more compact part, such as compressed Teflon graphite, on the outside, or the apparatus must be provided with some other tight outer wall.

In one embodiment, it is possible to use both this embodiment and other embodiments together with a series of enzymes, the product from one enzyme-catalysed process forming the substrate for the next enzyme-catalysed process. One or more of these coupled steps may utilize co-enzyme that can be regenerated with electrodes according to the present invention.

EXAMPLE 3

The surface 4 of a graphite rod 1, see FIG. 14, has been modified in accordance with this invention. It is surrounded by a dialysis membrane 5 which is covered by an O-ring 6. The membrane encloses a solution 3 which contains, in addition to a buffer, a soluble or matrix-bonded enzyme as well as a co-enzyme or co-enzyme analog. A counterelectrode 2 of graphite, platinum, or of the reference electrode type, is disposed on the outside of the dialysis membrane 5. The electrodes are immersed in a vessel 8 containing a buffered test solution 7. A voltage is applied between the electrodes 1 and 2. The voltage must be of such magnitude that the electrode surface 4 attains the potential required for reoxidizing the mediator functionalities of the surface.

If the test solution 7 contains substances capable of acting as a substrate to the enzyme at the electrode surface 4, a production of, for example, NADH from $NAD^+$ will take place when the substrate diffuses through the dialysis membrane. When NADH is then oxidized at the surface of the modified electrode, a current will pass through the circuit, and this current will be higher, the higher the substrate content of the sample 7.

By plotting a calibration curve for the solution 7 with known substrate contents, the apparatus can be utilized for analysing samples with unknown substrate contents. If the current is plotted as a function of the content of substrate, the calibration curve will be almost rectilinear over part of the working range of the method. Linearity and slope depend upon the co-enzyme content, the activity of the enzyme and the physical form of the enzyme layer and the stirring, if any, of the test solution. Such so-called enzyme electrodes have been described for other enzymes, whereas hydrogenases could be used in enzyme electrodes to a very limited extent only because of the difficulties of reproducibly reoxidizing the co-enzyme.

In one embodiment, also a reference electrode is immersed in the test solution or disposed close to the graphite electrode behind the dialysis membrane. The three electrodes are connected to a potentiostat. Potentiostatic checking of the electrode potential of the surface 4 improves the accuracy of measurement.

In one embodiment, the invention is utilized for analysing samples in an air-segmented or continuous flow. The samples are passed through a dialysis fibre 9. The electrode 10 according to this invention is given cylindrical shape, like the counterelectrode 11. They are sealed towards the dialysis fibres. Between the dialysis fibre and the modified electrode, there is provided a chamber 12 containing co-enzyme and enzyme. Between the counterelectrode and the dialysis fibre, a chamber 13 is provided which is filled with a liquid of good electric conductivity. If a sample 14 passes through the apparatus, a minor portion of any substrate in the sample will diffuse into the chamber 12 and generate a current therein, in the manner previously described. The magnitude of the current can be related to the content of the sample by calibration with solutions having a known substrate content.

In one embodiment of the invention for analysis of continuous or segmented flows, the sample can be advanced through a milled channel in a plastic block. A dialysis membrane is placed over the said channel, whereupon another block containing a graphite electrode according to the invention, a counterelectrode and, if desired, also a reference electrode is screwed into the first block to provide a seal. The electrodes of the latter block do not extend all the way up to the dialysis membrane, but leave room for enzyme and co-enzyme between the dialysis membrane and the electrode according to the invention, and also for a liquid film over the counterelectrode. If desired, channels can be drilled into the block so that solutions may be filled into the respective electrode spaces after assembly. In one embodiment for the analysis of flow systems, the channels are so designed that the dead volume will be small. In this manner, the apparatus can be used as a detector in chromatographic separation systems.

In another embodiment, conditions are so chosen that the enzyme reaction according to equation (1) cannot be fully displaced either to the right or to the left if the substrate content lies within the interval expected in the samples to be analysed. The position of the equilibrium is determined partly by thermodynamical data of the respective substrate and product, but may be affected by pH and, if necessary, a known excess of product may be added to all the samples. If an electrode according to the invention is immersed into a solution containing enzyme, co-enzyme or co-enzyme analog, substrate and product, a certain proportion of the mediator functionalities will be present in oxidized form and the remainder in reduced form. If the substrate content is changed, also the quotient between the oxidized and the reduced amount of mediator functionality will be displaced. The electrode potential—in the absence of current—of the modified electrode will thus be changed according to Nernst's formula $E = E° + (RT/zF) \cdot \ln\{(Ox)/(Red)\}$. The electrode potential can be measured relative to a reference electrode of conventional type by means of a pH-meter or an electrometer. In actual practice, the apparatus preferably is devised in the manner previously described in connection with FIG. 13, but with the difference that the counterelectrode is replaced by a reference electrode. The difference resides in the function, not in the construction. The substrate should diffuse through the dialysis membrane until equilibrium has been established. The equilibrium is not disturbed electrolytically, but is sensed potentiometrically. In flow systems, however, it is not always necessary to wait until full equilibrium has been established. An almost rectilinear calibration curve is obtained if the potential is plotted against the logarithm of the substrate content. The adjustment of equilibrium towards a reduced substrate content can be accelerated if a catalyst for the reaction of types (5) and (8) from right to left is introduced into the solution outside the modified electrode surface. Examples of such catalysis are enzymes of various types. A different hydrogenase with its associated substrate and product may also be introduced and dimensioned such that $NAD^+$ is continuously and very slowly converted into NADH.

EXAMPLE 4

FIG. 15 illustrates how the electrodes according to this invention can be designed for use with biochemical fuel cells for production of electric energy. The porous graphite electrode 1 has been devised in accordance with the invention. The cathode 2 consists of, for example, an oxygen electrode of known type. If oxygen is used, it is introduced through 3, and the excess is discharged through 4. In this embodiment, the electrode 2 consists of graphite prepared in such a way that the oxygen can diffuse through the electrode material up to the boundary layer to the electrolyte 5. The graphite surface is coated with a catalyst of known type, for instance phthalocyanines with a suitable metal as the central atom. The electrode 2 (the cathode) is designed for instance in the form of a cylindrical disk, like the electrode 1 according to the invention. The distance therebetween is short in order to reduce the ohmic voltage drop. The electrolyte 5 must have good conductivity, a high content of co-enzyme and may contain organic or inorganic cations thereby to further reduce the overvoltage. Furthermore, the fuel cell is equipped with a pump 6 pumping the electrolyte through one or more enzyme reactors 7, 8 and then back to the electrode space. Means for supplying fuel and discharging the reaction product (such as carbon dioxide and water) are also required, but these are not shown in the Figure.

A cell constructed to operate with alcohol as a fuel, contains alcohol dehydrogenase in the reactor 7. The resulting aldehyde may either be regarded as the final product and can be removed, or it can be oxidized in a further step of aldehyde dehydrogenase in the enzyme reactor 8. These oxidations are effected with hydrogenases, and one mole of NADH is formed in the reactor 7 for each mole of oxidized alcohol. If two enzymes are used, two moles of NADH are formed per mole of alcohol. The resulting reduced co-enzyme is capable of transferring mediator functionalities to the surface of the modified graphite electrode 1 in reduced form. The electrode will assume a negative potential (the oxygen electrode has a positive potential). The current is generated by oxidation of reduced mediator functionalities which, however, are again reduced by NADH in the electrolyte so tat the half-cell can continue its supply of current. However, NADH is produced, according to need, from alcohol in the electrolyte in the enzyme reactors. In view hereof, the net reaction in the entire fuel cell will be with, for example, methanol as fuel and two enzyme systems, $$CH_3OH + O_2 \rightarrow HCOOH + H_2O \qquad (11)$$

four moles of electrons being driven around the circuit for each mole of oxygen and method consumed. With three enzyme systems, the final product will be carbon dioxide and water.

Theoretically, the efficiency of the fuel cell can be much higher than by the roundabout way employing mechanical heat machines. Alreadly at the present development stage, the efficiency of the fuel cell described above is at least as good as that of the heat machines (at current intensities of a few milliamperes per square centimeter of electrode surface). The terms anode and cathode indicate whether the electrode reaction is an oxidation or a reduction, respectively. The fuel cell generates a net current. In the other applications described above, the apparatus has consumed current for supplying, for example, a synthesis product. In view hereof, the current reactions and terms will be inverse.

We claim:

1. An electrode for the electrochemical regeneration of coenzymes dihydronicotinamide adenine dinucleotide (NADH), dihydronicotinamide adenine dinucleotide phosphate (NADPH), or analogs thereof, characterized in that it comprises carbon or a graphitic material to the surface of which is adsorbed a condensed aromatic ring system comprising phenoxazinium ions, phenoxazinones, phenothiazinium ions or phenothiazinones, substituted or unsubstituted.

2. An electrode as claimed in claim 1, characterized in that one or more enzymes, at least one of which is of the dehydrogenase type, are present in dissolved, suspended or immobilized form on or at the electrode surface, an that NADH or NADPH or analogs thereof have been applied in dissolved or immobilized form, whereby said coenzyme can be reoxidized by the electrode.

3. An electrode as claimed in claim 2, characterized in that the enzyme or enzymes are retained in the vicinity of said electrode by a membrane permeable to small molecules.

4. An electrode as claimed in claim 1, characterized in that one or more enzymes, at least one of which is of the dehydrogenase type, have been immobilized and applied such that the coenzymes or coenzyme analogs can be conveyed between the enzyme bed and the electrode surface.

5. An electrode as claimed in claim 1, characterized in that the active ring system on the electrode surface can be replenished from reservoirs in or on the electrode material, or from a solution of the substances or on the ions in the working electrolyte in low contents.

6. A method of making an electrode for the electrochemical regeneration of the coenzymes dihydroicotinamide adenine dinucleotide (NADH), dihydronicotinamide adenine dinucleotide phosphate (NADPH), or analogs thereof, characterized in that there is adsorbed to the surface of the electrode which consists of carbon or a graphitic material a condensed aromatic ring system comprising phenoxazinium ions, phenoxasinones, phenothiazinium ions or phenothiazinones, substituted or unsubstituted.

7. In a method of electrochemical regeneration of coenzymes for biotechnical, microbiological, or biochemical purposes, the steps of providing an electrode comprising carbon or a graphitic material to the surface of which is adsorbed a condensed aromatic ring system comprising phenoxazinium ions, phenoxazinones, phenothiazinium ions or phenothiazinones, substituted or unsubstituted, and employing said electrode in an electrochemical cell for the regeneration of coenzymes dihydronicotinamide adenine dinucleotide (NADH), dihydroniciotinamide adenine dinucleotide phosphate (NADPH), or analogs thereof.

8. A method of improving the performance of a biochemical fuel cell which operates with dehydrogenases as catalysts and with coenzyme as energy-transferring redox pair, which comprises providing an electrode comprising carbon or a graphitic material to the surface of which is adsorbed a condensed aromatic ring system comprising phenoxazinium ions, phenoxazinones, phenothiazinium ions or phenothiazinones, substituted or unsubstituted, and operating said fuel cell with said electrode serving as the anode thereof.

9. A method of analysis in systems utilizing coenzyme-dependent enzyme, the comprises providing an electrode comprising carbon or a graphitic material to the surface of which is adsorbed a condensed aromatic ring system comprising phenoxazinum ions, phenoxazinones, phenothiazinium ions or phenothiazinones, substituted or unsubstituted, and employing said electrode in an analytical apparatus in which coenzymes dihydronicotinamide adenine dinucleotide (NADH), dihydronicotinamide adenine dinucleotide phosphate (NADPH), or analogs thereof are generated.

* * * * *